United States Patent [19]

Mulligan

[11] Patent Number: 4,950,291
[45] Date of Patent: Aug. 21, 1990

[54] BREAST PROSTHESIS

[75] Inventor: Elisabeth Mulligan, Söllhuben, Fed. Rep. of Germany

[73] Assignee: Amoena Corporation, Marietta, Ga.

[21] Appl. No.: 272,069

[22] Filed: Nov. 16, 1988

[30] Foreign Application Priority Data

Dec. 14, 1987 [DE] Fed. Rep. of Germany ....... 3742352

[51] Int. Cl.$^5$ .............................................. A61F 2/12
[52] U.S. Cl. ......................................... 623/8; 623/6; 623/7
[58] Field of Search .................................. 623/6, 7, 8

[56] References Cited

U.S. PATENT DOCUMENTS

| | | |
|---|---|---|
| 2,543,499 | 2/1951 | Kausch . |
| 2,580,264 | 12/1951 | Wright et al. . |
| 2,651,783 | 9/1953 | Wright et al. . |
| 2,814,808 | 12/1957 | Berman . |
| 2,962,767 | 12/1960 | Trojanowski et al. . |
| 3,048,169 | 8/1962 | Pierce . |
| 3,067,431 | 12/1962 | Kausch . |
| 3,196,464 | 7/1965 | McKee . |
| 3,494,365 | 2/1970 | Beals ........................................ 623/8 |
| 4,086,666 | 3/1978 | Vaskys et al. . |
| 4,172,298 | 10/1979 | Rechenberg . |
| 4,185,332 | 1/1980 | Jahnig . |
| 4,247,351 | 1/1981 | Rechenberg . |
| 4,249,975 | 2/1981 | Rechenberg . |
| 4,317,241 | 3/1982 | Knoche . |
| 4,600,551 | 7/1986 | Erb . |
| 4,676,795 | 6/1987 | Grundei . |
| 4,681,587 | 7/1987 | Eber et al. .............................. 623/7 |
| 4,701,230 | 8/1987 | Loi . |
| 4,795,464 | 1/1989 | Eber et al. .............................. 623/8 |

FOREIGN PATENT DOCUMENTS

| | | |
|---|---|---|
| 272327 | 11/1965 | Australia . |
| 461084 | 12/1970 | Australia . |
| 2605148 | 11/1977 | Fed. Rep. of Germany . |

OTHER PUBLICATIONS

*Nearly Me* ®, Ruthton Corporation.
*Tru–Life Silicon Model* #236, Tru-Life, Inc.
*Comfort* 2000 Silicon Breast Prosthesis, Bodo Knoche Corporation.
*Melody*, Knoche Natural Corporation.
*Knoche Custom Made Breast Prosthesis*, Bodo Knoche Corporation.
Patzke and Wohlfarth, "*Vernetzungssysteme beim Siliconkautschuck*", 97th year (1973), No. 4, pp. 176–180.

Primary Examiner—Richard J. Apley
Assistant Examiner—N. Paul
Attorney, Agent, or Firm—Jones, Askew & Lunsford

[57] ABSTRACT

An external breast prosthesis is disclosed including two shell shaped chambers containing silicone rubber material of different softness. The silicone rubber material is confined by outer front and back polyurethane films, and the chambers are divided by an intersitial film. The films are welded together along their common peripheral edge. The silicone rubber in the back chamber which is placed next to the chest wall is softer than that in the front chamber, and conforms to the shape of the chest wall following surgery.

16 Claims, 1 Drawing Sheet

U.S. Patent    Aug. 21, 1990    4,950,291
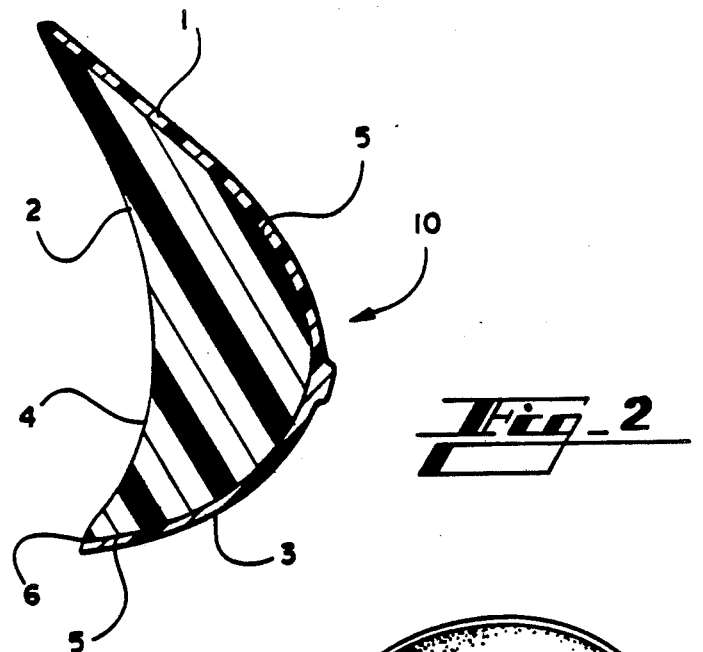
Fig_2
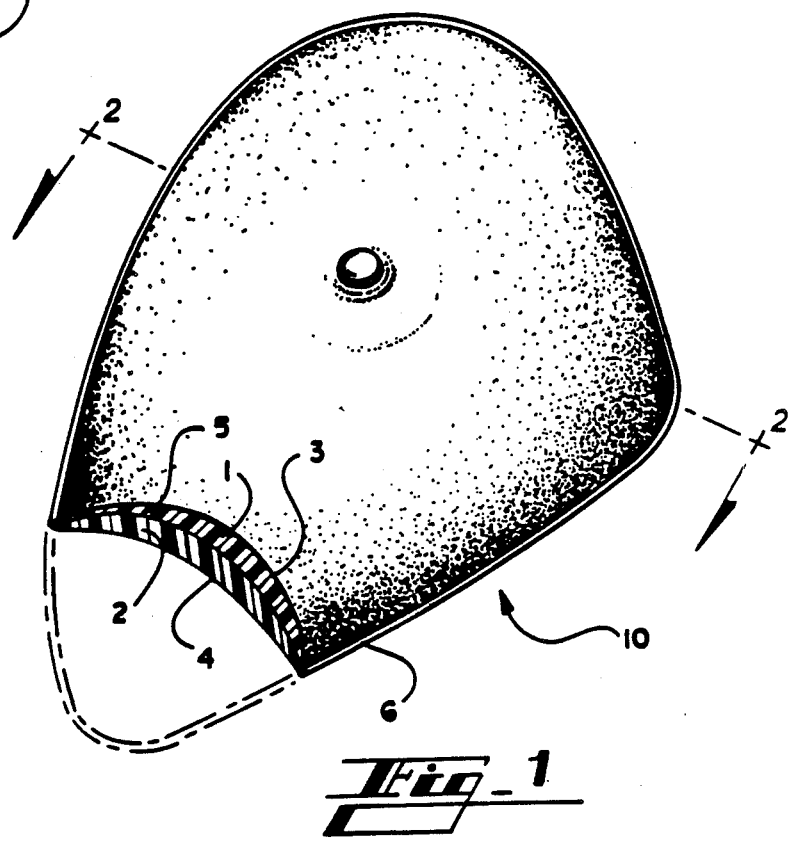
Fig_1

BREAST PROSTHESIS

TECHNICAL FIELD

This invention involves a breast prosthesis consisting of two shell shaped components made of a meshing two component silicone rubber material of varying softness whose plastic wrappings of the external and interior sides are welded along their entire common edge with another plastic film separating the two components.

BACKGROUND ART

German patent DE-AS 26 05 148 already specifies a breast prosthesis of this type which, however, only has one shell shaped component welded in plastic films and made of a meshing two component silicone rubber material. Women in general greatly appreciate this breast prosthesis, since the cured two component silicone rubber material corresponds in its weight approximately to the weight of the natural breast tissue and since the unit made of the two component silicone rubber material manages to simulate in almost a perfect fashion the actual conditions of the natural breast due to its soft elastic responsiveness and mobility. Breast prosthesis of this type are inserted in brassieres for support. U.S. Pat. Nos. 4,172,298 and 4,249,975, both of which are incorporated herein by reference, disclose this type of prosthesis.

In order to assure the most natural appearance of the breast prosthesis when inserted in the brassiere, it is common practice in a breast prosthesis of the type described above for a body forming the convex exterior side to be made of a soft set material while a flat shell shaped body forming the back side of the prosthesis is made of a slightly harder set two component silicone rubber material.

The result of this design is that the elastically soft and due to its weight slightly sinking convex external side of the breast prosthesis is supported by its rear side made of stiffer material.

The disadvantage of the known breast prosthesis type due to the inner layer or inner shell of harder two component silicone rubber material is that this inner shell presses on the sensitive scar tissue area and it does not adjust in the required protective fashion to that area.

Thus the invention is directed to solving problems with external breast prosthesis known prior to the invention. These prostheses have not been adaptable to fit irregularities in the chest of the mastectomy patient, particularly as modern surgical techniques remove less tissue and leave more irregular chest wall contours. Although matching the chest wall contours has been accomplished by custom-molding of a prosthesis for each patient, a need exists for a prosthesis that has desirable characteristics of appearance and touch, but can adapt to the chest wall contours of many different patients.

It is the task of this invention to develop a breast prosthesis of the type specified above whose wearing comfort is enhanced so substantially that it adjusts ideally to the scar tissue area.

SUMMARY OF THE INVENTION

According to this invention, the task is handled by a breast prosthesis of the type specified in general terms above having an external component which mimics the breast shape with a hardness correlating to the soft elastic responsiveness of the natural breast tissue while the inner body has a soft gel-like consistency. Contrary to present opinion, whereby the frontal area of the prosthesis must be supported by a rear shell-shape component of greater hardness, the breast prosthesis according to the invention fabricates this rear component precisely of a softer material of gel-like consistency. The inner shell shaped component thus due to its gel-like consistency is so soft that it adjusts perfectly to the scar area exerting absolutely no pressure on it. Thereby the wearing characteristics of the breast prosthesis have been substantially improved. Surprisingly, we found that despite the softer design of the inner shell, the appearance of the breast prosthesis inserted in the brassiere does not suffer so that it retains its natural look.

Somewhat more particularly described, the invention is a breastform having two chambers or shells defined by three polyurethane films welded together at their outer peripheries. The chamber closest to the wearer's chest is filled with a soft silicone gel. The chamber forming the outer layer of the breastform is filled with a relatively stiff silicone gel and is thinner than the inner chamber. The stiffer outer layer maintains the shape of the breast form and prevents the outermost polyurethane film from wrinkling. The soft inner silicone can flow into cavities in the chest wall in order to conform to the contours left after surgery. The "feel" of the breastform is realistic because the outer layer can move to the touch by displacing the soft inner silicone gel. The stiffness of the outer layer gel can be varied, so that the thickness of the outer layer is decreased as the stiffness of the gel is increased. The stiffness and thickness are adjusted to produce the desired "feel" of the prosthesis.

Thus, it is an object of the present invention to provide an improved external breast prosthesis.

It is a further object of the present invention to provide an external breast prosthesis which conforms to the contours of the chest wall following mastectomy surgery, while maintaining at its outer surface the shape of a breast.

It is a further object of the present invention to provide an external breast prosthesis having an external surface which maintains a desirable shape, has a realistic feel to the touch, and which resists wrinkling.

Other objects, features, and advantages of the invention will become apparent upon review of the following detailed description of an embodiment of the invention, when taken in conjunction with the drawing and the appended claims.

BRIEF DESCRIPTION OF THE DRAWING

FIG. 1 is a front pictorial view of a breast prosthesis embodying the present invention, with a portion broken away to show interior detail.

FIG. 2 is a cross sectional view of the prosthesis of FIG. 1, taken along line 2—2 of FIG. 1.

DETAILED DESCRIPTION

Referring now in more detail to the drawing, in which like numerals refer to like parts throughout the several views, FIG. 1 shows a breast prosthesis 10 embodying the present invention.

The drawing shows a breast prosthesis 10 which has been partially cut away. The breast prosthesis consists of an external convex shell component 1 of a soft set meshing two component silicone rubber material and a component 2 forming the backside of the prosthesis in the form of a shell which is made of an even softer setting gel-like material of meshing two component silicone rubber. Both components 1 and 2 are enclosed on their external side by polyurethane films 3 and 4 and separated from each other by interstitial film 5 also made of polyurethane. All three films are linked by a joint seam weld 6 along the outer edge of the prosthesis. Polyurethane is the preferred film material, although other plastic films may be used.

Preparation of the silicon rubber material forming the components 1 and 2 is within the expertise of those skilled in the art. An appropriate silicone rubber is described in detail in Patzke and Wohlfarth, "Vernetzungssysteme beim Siliconkautschuk," in CHEMIKER-ZEITUNG 97th year (1973) No. 4, pages 176–180, which is incorporated herein by reference. The relative stiffness of the two components may be selected as desired to provide the advantages described herein. Preferably, the silicone rubber material forming the component 1 has a penetration measured in a range from 20.0 to 24.0 mm, and the component 2 has a penetration above 30.0 mm. These values represent measurements with a "Precision" penetrometer using a 15 gram cone having an aluminum tip of height 0.6 inch and base diameter 0.33 inch, and a plastic cone body extending 1.13 inches from the tip base and having a base diameter of 2.56 inches. Preferably, the thickness of the component 1 is approximately 10–30 percent of the thickness of the softer component 2 at its thickest location. For example, the component 1 may be approximately one quarter inch thick, whereas the thickest dimension of the component 2 may be 0.8–2.5 inches thick.

The breast prosthesis according to the invention can be manufactured the following way:

Between the plastic films 3 and 4 forming the breast prosthesis there is an interstitial film 5 which is welded jointly with the external films along the future breast prosthesis edge with the exception of a fill opening. First, the films are placed in a mold having a surface similar to the shape of a breast, and between the film 3 forming the convex external side of the breast prosthesis and the interstitial film 5, a soft set two component silicone rubber material is filled in. Between the other two films 4 and 5 a separating medium is filled in to prevent their welding or blocking. After the mold is closed with another mold component whose shape corresponds to the inner side of the shell 1, the material is cured. Subsequently a gel-like two component silicone rubber material is filled in between the other films 4 and 5. After closing with an upper mold component whose shape corresponds with the back side of the prosthesis, the shell 2 made by the second filling cycle is cured.

While this invention has been described with particular reference to preferred embodiments thereof, it will be understood that variations and modifications can be made without departing from the spirit and scope of the invention as described hereinbefore and as defined in the appended claims.

I claim:

1. An external breast prosthesis, comprising:
   a breast member comprising an inner layer of soft, flowable gel-like elastic material capable of conforming to irregularities in the chest of a wearer, and an outer layer of elastic material, said outer layer being stiffer than said inner layer.

2. The prosthesis of claim 1, wherein said outer layer is thinner than said inner layer.

3. The prosthesis of claim 2, further comprising a wall of film separating said inner layer and said outer layer.

4. The prosthesis of claim 3, wherein said outer layer is sufficiently soft to yield to the touch.

5. The prosthesis of claim 1, wherein said inner layer and said outer layer are each confined by a film envelope.

6. The prosthesis of claim 5, wherein said film envelopes comprise polyurethane.

7. The prosthesis of claim 3, wherein said elastic materials comprise silicone materials.

8. The prosthesis of claim 5, wherein said outer layer is sufficiently stiff to substantially prevent wrinkling of said film envelope confining said outer layer and said outer layer is sufficiently soft to yield to the touch.

9. The prosthesis of claim 1, wherein said outer layer is sufficiently stiff to generally retain the shape of a human breast.

10. The prosthesis of claim 1, wherein said outer layer is approximately 10–30% of the thickness of said breast member at its thickest location.

11. A breast prosthesis comprising:
   two shell shaped components made of a meshing two component silicone material of varying softness;
   plastic film wrappings of the exterior and interior sides of said components are welded together, and
   an interstitial plastic film separating the two components along their common encircling edge;
   the outer edge of said components mimicking the breast shape and having a hardness which imitates the soft elastic responsiveness of natural breast tissue, and the inner of said components having a soft, flowable gel-like consistency capable of conforming to irregularities in the chest of a wearer.

12. A method of making a breast prosthesis, comprising the steps of:
   welding together three plastic films along the edge of the prosthesis;
   inserting between two of said films an outer elastic material;
   inserting between said third film and the film adjacent thereto an inner soft, flowable gel-like elastic material capable of conforming to irregularities in the chest of a wearer, said third film forming the back of said prosthesis to be placed against the chest of a wearer.

13. The prosthesis of claim 7, wherein said silicone material of said inner layer comprises silicone gel.

14. The breast prosthesis of claim 1, wherein said stiffer outer layer is spaced from the chest of a wearer by said inner layer.

15. The breast prosthesis of claim 5, wherein said film envelope confining said inner layer conforms to irregularities in the chest of a wearer with said soft, flowable gel-like elastic material of said inner layer.

16. The prosthesis of claim 1, wherein said material of said outer layer has a penetration in a range from about 20.0 to about 24.0 mm, and said material of said inner layer has a penetration of at least about 30 mm.

* * * * *